United States Patent [19]

Menchel et al.

[11] Patent Number: 4,968,310
[45] Date of Patent: Nov. 6, 1990

[54] APPLICATOR FOR LIQUID EYE PREPARATIONS

[76] Inventors: Jehoshua Menchel; Malka Menchel, both of 23, Yakinton St., Yavne 70 600, Israel

[21] Appl. No.: 379,610

[22] Filed: Jul. 13, 1989

[30] Foreign Application Priority Data

Jun. 27, 1989 [IL] Israel .................................. 90763

[51] Int. Cl.⁵ ............................................. A61M 35/00
[52] U.S. Cl. ................................... 604/295; 604/300; 222/206
[58] Field of Search ............... 604/294, 295, 298, 299, 604/300, 301, 302; 222/420, 421, 206, 207

[56] References Cited

U.S. PATENT DOCUMENTS

| | | | |
|---|---|---|---|
| 2,083,156 | 6/1937 | McCabe | 222/207 |
| 2,789,734 | 4/1957 | Biederman | 222/420 |
| 3,439,674 | 4/1969 | Lelicoff | 604/302 |
| 4,629,456 | 12/1986 | Edwards | 604/300 |
| 4,733,802 | 3/1929 | Sheldon | 222/181 |

FOREIGN PATENT DOCUMENTS

| | | | |
|---|---|---|---|
| 8768247 | 12/1987 | Australia . | |
| 269337 | 10/1950 | Italy | 604/295 |

Primary Examiner—John D. Yasko
Assistant Examiner—C. Maglione
Attorney, Agent, or Firm—Steinberg & Raskin

[57] ABSTRACT

An application for liquid ophthalmic solution is provided which has a laterally protruding spout and a resiliently flexible wall portion. Application of ophthalmic solution to the eye is performed by placing the tip of the nozzle on the lower eyelid and by applying pressure to the flexible wall portion, whereupon the ophthalmic solution flows directly into the eye.

8 Claims, 1 Drawing Sheet

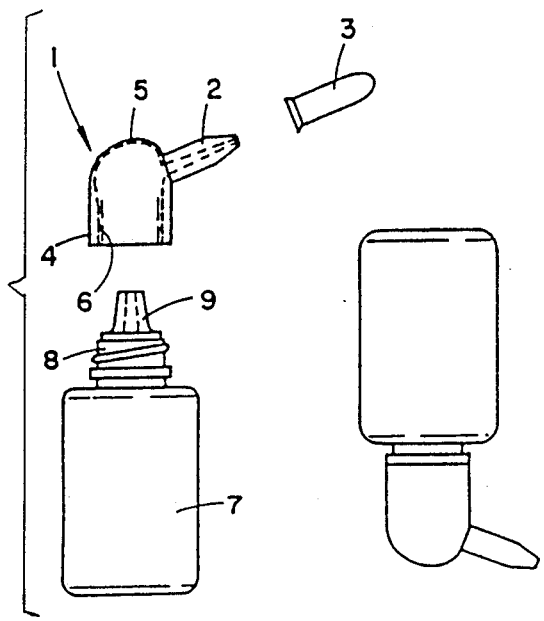
Fig. 1　Fig. 2
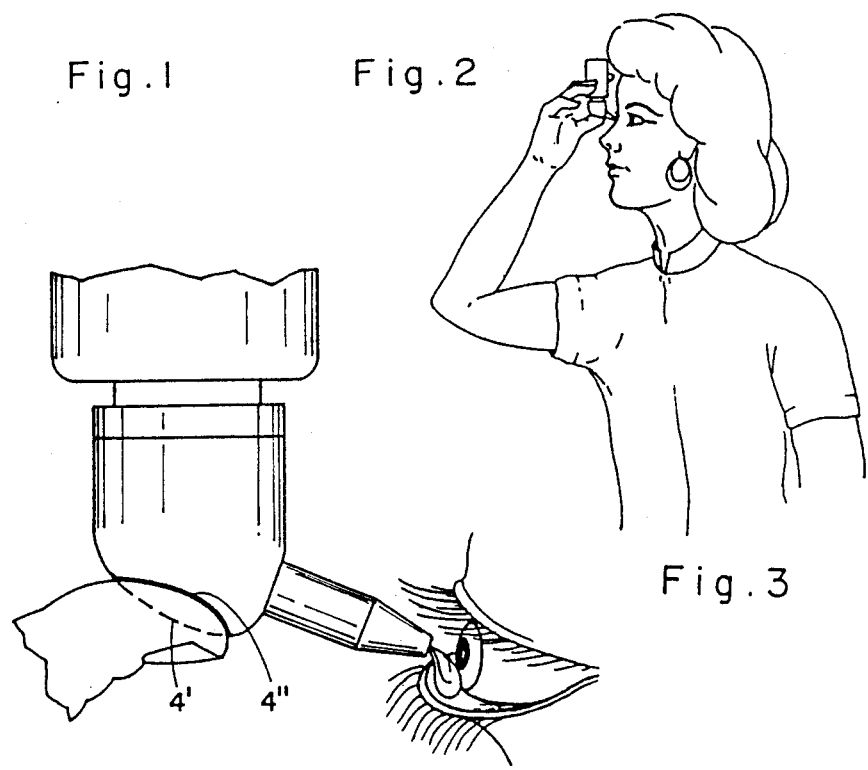
Fig. 4
Fig. 3

APPLICATOR FOR LIQUID EYE PREPARATIONS

FIELD AND BACKGROUND OF THE INVENTION

The present invention is in the field of self administration of medicated ophthalmic solutions to be referred to hereinafter for short as "eye liquid".

Eye liquids are generally administered in the form of drops. Conventionally, dropper bottles are used, and for self administration the user has to recline his head, bring the nozzle of the dispensing bottle directly above the eye and then release a given number of drops. By prescribing the number of drops, the doctor can determine the dose for each administration.

Experience shows that such a mode of administration is not that easy to perform and may be rather tricky in that very often a fair proportion of eye liquid is wasted in that drops do not fall directly into the eye in consequence of improper aiming. This is particularly true for people with poor eyesight, poor motor coordination or both, such as, for example, blind and elderly people who for that reason may be precluded from self administration and require assistance of another person.

Apart from the inconvenience that it causes, inaccurate administration may also be economically burdensome due to the fact that eye liquid may be rather expensive so that waste due to improper administration gives rise to substantial increase in the cost of the medical treatment.

U.S. Pat. No. 4,629,456 discloses an eye solution dropper bottle which has a conical nozzle comprising a contrasting target ring applied to a portion of the nozzle which enables proper positioning of the orifice in the centre of the eye. The drawback of this bottle is that its use requires good eyesight and it is thus not suitable for people with poor eyesight or whose eyesight is temporarily impaired due to a pathological condition.

In AU-A-68247/87 there is described an aid for administration of eye drops having the form of a small, handleless cup-shaped transparent cylinder, one side of which has a size and shape which enables it to be fitted against the eyebrows of the human eye, the other side thereof having a small opening in its centre into which a nozzle of a dispensing bottle may be inserted.

A somewhat similar eye drop dispensing device is described in U.S. Pat. No. 4,733,802. In accordance with that patent there is provided a bottle support having a transparent sloping wall surface and an opening through which the patient may insert a finger to retract the lower eyelid and maintain it in an open position while the eye drop is being dispensed. This overcomes the problem of reflex in closing of the eyelids upon application of drops as will occur with the device of AU-A-68247/87. However, with the device of the aforementioned U.S. patent exact targeting is necessary which may on some occasions be difficult for reasons explained above.

SUMMARY OF THE INVENTION

It is the object of the present invention to provide an applicator for eye liquid which does not require eyesight or any other means for proper targeting of the solution to the eye.

In accordance with the invention there is provided an eye liquid applicator adapted to be mounted on the opening of an eye liquid holding bottle, comprising a hollow body having a cylindrical wall portion opened at one end and a dome shaped end wall portion at the opposite end. One of the said wall portions or a part thereof being resiliently flexible. Said applicator further comprising a spout protruding laterally from a non resilient wall portion.

In use, the applicator is mounted onto the opening of an eye liquid holding bottle and before operation the resulting assembly is inversed with the applicator down. Preferably, the laterally protruding spout is off the horizontal plane so that in operation it assumes a slightly downward slant.

In accordance with the invention it is preferred that the resiliently flexible wall portion or part thereof will be at the end wall portion.

BRIEF DESCRIPTION OF THE DRAWINGS

In the following the invention will be described, by way of example only, with reference to the annexed drawings in which:

FIG. 1 is an exploded view of an assembly consisting of an applicator according to the invention, shown in cross section, an eye liquid containing a bottle and a spout covering cap;

FIG. 2 shows the assembly of FIG. 1 in the fully assembled state and in operative position;

FIG. 3 is a pictorial view of a woman in the course of self-administration of eye liquid using the bottle-applicator assembly of FIG. 2;

FIG. 4 is a partial view of FIG. 3 drawn to a larger scale and illustrating the mode of operation.

DESCRIPTION OF A SPECIFIC EMBODIMENT

The applicator 1 according to the invention shown in FIG. 1 is a cup-shaped hollow body and comprises a slightly slanted, essentially sideways protruding spout 2. A cap 3 serves for mounting on spout 2 when the applicator is not in use. The hollow body has a cylindrical wall portion 4 open at one end and merging at the opposite end into a dome shaped end wall portion 5. Applicator 1 is internally screw-threaded at 6, and thereby adapted for mounting on an externally screw-threaded neck portion 8 of a bottle 7. The applicator 1 may be made of any one of a large number of polymeric materials such as polyethylene, polypropylene, PVC and the like, and is preferably transparent or translucent. As shown in FIG. 1, the end wall portion 5 of the applicator is relatively thin walled as compared to the cylindrical wall portion 4 and is thereby rendered resiliently flexible.

As shown, the eye liquid dispensing bottle 8 is of conventional design and comprises a nozzle 9 and is thereby adapted for use as a conventional eye dropper bottle. When bottle 8 is used in conjunction with an applicator 1 according to the invention, nozzle 9 may optionally be removed so that upon inversion of the assembly as shown in FIGS. 2 to 4, the eye liquid fills the applicator.

It should be noted that in addition to screw-mounting, the applicator of the invention may also engage an eye liquid bottle in any other suitable manner such as by means of a male-female type locking assembly, e.g. a resilient catch type lock, a bayonet catch type lock and the like.

As shown in FIGS. 3 and 4, the dome shaped end wall portion 5 of applicator 1, yields upon the application of pressure, whereby an amount of liquid is ejected via the spout 2 into the eye. Upon pressure release end wall portion 5 returns to its relaxed state.

As shown in FIG. 3, the administration of eye liquid with the aid of an applicator according to the invention, is simple and may be performed even by individuals with poor eyesight. During application the head is kept in the normal position, the tip of spout 2 is brought to bear onto the lower eyelid and upon application of some pressure onto the resilient wall portion 5 of applicator 1, eye liquid flows directly into the eye.

The amount of applied eye liquid depends on the resiliently flexible wall portion 5. Upon depression of part of the dome shaped end wall portion 5 in the manner shown in FIG. 4, resistance to further depression is increased. Use is made of this feature for dosing the administered eye liquid in that once the increase of resistance is felt by the user the application is discontinued and in this way the amount of liquid in each application remains substantially the same.

We claim:

1. An eye liquid applicator adapted to be mounted on the opening of an eye liquid holding bottle, comprising a hollow body having a cylindrical wall portion opened at one end and a dome shaped end wall portion at the opposite end, an integral laterally protruding rigid spout comprising a base situated on a lateral part of the applicator adjacent to the area of contact between said cylindrical wall portion and said end wall portion, a part of said end wall portion being adjacent to the base of said spout being resiliently flexible and all other parts of said end wall portion and the cylindrical wall portion being non-resilient.

2. An applicator according to claim 1, wherein the spout protrudes from said non resilient wall portion with a slant.

3. An applicator according to claim 1, being transparent or translucent.

4. An applicator according to claim 1, wherein the cylindrical wall portion is internally screw-threaded and thereby adapted for screwing onto an externally screw-threaded neck portion of bottle.

5. An applicator according to claim 1, wherein the cylindrical wall portion is adapted for engagement of the said eye liquid holding bottle by means of a male-female type locking assembly.

6. An eye liquid dispensing assembly comprising a bottle and an eye liquid applicator adapted to be mounted on the opening of said bottle, said applicator comprising a hollow body having a cylindrical wall portion opened at one end and a dome shaped end wall portion at the opposite end, and said applicator further comprising an internal laterally protruding rigid spout comprising base situated in a lateral part of said applicator adjacent to the zone of contact between said cylindrical and said end wall portions, a part of said end wall portion not being adjacent to the base of said spout being resiliently flexible and all other parts of said end wall portion and cylindrical wall portion being non-resilient.

7. An eye liquid applicator to claim 1 wherein the resiliently flexible part of the end wall portion is capable of being depressed by a finger of the user.

8. An eye liquid applicator according to claim 7 wherein the amount of the liquid to be applied is limited by the initial curvature and the flexibility of the resiliently flexible part of the end wall portion.

* * * * *

UNITED STATES PATENT AND TRADEMARK OFFICE
CERTIFICATE OF CORRECTION

PATENT NO. : 4,968,310

DATED : November 6, 1990

INVENTOR(S) : Yehoshua MENCHEL, et al.

It is certified that error appears in the above—identified patent and that said Letters Patent is hereby corrected as shown below:

Column 3, line 24, Claim 1, should read as follows:

1. An eye liquid applicator adapted to be mounted on the opening of an eye liquid holding bottle, comprising a hollow body having a cylindrical wall portion opened at one end and a dome shaped end wall portion at the opposite end, an integral laterally protruding rigid spout comprising a base situated on a lateral part of the applicator adjacent to the area of contact between said cylindrical wall portion and said end wall portion, a part of said end wall portion not being adjacent to the base of said spout being resiliently flexible and all other parts of said end wall portion and the cylindrical wall portion being non-resilient.

Signed and Sealed this

Thirty-first Day of December, 1991

Attest:

HARRY F. MANBECK, JR.

Attesting Officer     Commissioner of Patents and Trademarks